United States Patent [19]

Singer et al.

[11] Patent Number: 4,501,854
[45] Date of Patent: Feb. 26, 1985

[54] AMINOPLAST CURABLE COMPOSITIONS CONTAINING DISULFONIC ACID ESTERS AS LATENT ACID CATALYSTS

[75] Inventors: Debra L. Singer, Pittsburgh; Gregory J. McCollum, Glenshaw; Rostyslaw Dowbenko, Gibsonia, all of Pa.

[73] Assignee: PPG Industries, Inc., Pittsburgh, Pa.

[21] Appl. No.: 551,388

[22] Filed: Nov. 14, 1983

[51] Int. Cl.³ ............................................. C08L 61/28
[52] U.S. Cl. ................................ 525/162; 525/329.4; 525/353; 525/442; 525/443; 525/456; 525/480
[58] Field of Search .............. 525/162, 218, 134, 442, 525/443, 456, 480, 329.4, 353; 528/487; 252/426

[56] References Cited

U.S. PATENT DOCUMENTS

| | | | |
|---|---|---|---|
| 2,141,893 | 12/1938 | Zitscher et al. | 260/505 |
| 2,227,708 | 1/1941 | Cordier | 260/71 |
| 2,631,138 | 3/1953 | Dannenberg | 260/45.2 |
| 2,961,424 | 11/1960 | Mueller et al. | 260/45.2 |
| 3,079,434 | 2/1963 | Christenson et al. | 525/110 |
| 3,293,324 | 12/1966 | Tropp et al. | 260/850 |
| 3,384,606 | 5/1968 | Dieterich et al. | 260/29.4 |
| 3,474,054 | 10/1969 | White | 260/15 |
| 3,732,273 | 5/1973 | Heine et al. | 260/456 R |
| 3,798,262 | 3/1974 | Ziegler et al. | 260/505 R |
| 3,840,591 | 10/1974 | Lee et al. | 260/505 R |
| 3,842,021 | 10/1974 | Grant et al. | 260/15 |
| 3,907,706 | 9/1975 | Robins | 252/431 C |
| 3,979,478 | 9/1976 | Gallacher | 260/850 |
| 4,075,176 | 2/1978 | Gallacher | 260/67.6 R |
| 4,083,830 | 4/1978 | Gallacher | 260/67.6 R |
| 4,192,826 | 3/1980 | Beresniewicz et al. | 525/425 |
| 4,200,729 | 4/1980 | Calbo | 525/398 |
| 4,247,461 | 1/1981 | Lin et al. | 260/239.1 |
| 4,281,075 | 7/1981 | Chattha | 525/110 |
| 4,350,790 | 9/1982 | Chattha | 525/110 |

FOREIGN PATENT DOCUMENTS

| | | |
|---|---|---|
| 0033038 | 8/1981 | European Pat. Off. |
| 2229364 | 1/1974 | Fed. Rep. of Germany |
| 56-3357 | 4/1982 | Japan |
| 56-3358 | 4/1982 | Japan |
| 1361929 | 7/1974 | United Kingdom |
| 1413054 | 11/1975 | United Kingdom |
| 1560821 | 2/1980 | United Kingdom |

OTHER PUBLICATIONS

Matar & Mekkawy, "The Effect of Ring Size and 2-Methyl Substituents on the Rate of Elimination of Cycloalkyl Tosylates in Dimethyl Sulphoxide", Indian J. Chem., vol. 13, May 1975, pp. 530–531, and vol. LI, Sep. 1974, pp. 839–840, published by Counsel of Scientific & Ind. Research, Publ. & Inf. Directorate, Hillside Rd., New Delhi, India 110012.

Kotani, "Pyrolysis & Acetolysis of Some Sulfonic Esters", Bulletin of the Chemical Society of Japan, vol. 39, Aug. 1966, pp. 1767–1773, publ. by Chemical Society of Japan-Nippon, 5 1-chome, Kanda-Surugadai, Chiyoda-ku, Tokyo, Japan 101.

Primary Examiner—Theodore E. Pertilla
Attorney, Agent, or Firm—Linda Pingitore

[57] ABSTRACT

An improved curable composition capable of acid catalyzed crosslinking is composed of an active hydrogen-containing resin, a curing agent and a sulfonate as latent acid catalyst. The catalyst is represented by the following structural formula:

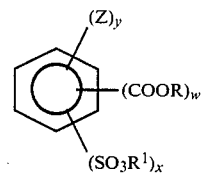

wherein:
Z is a radical independently selected from $C_1$ to $C_{20}$ alkyl, $C_3$ to $C_{20}$ cycloalkyl, $C_6$ to $C_{18}$ aryl, halogen, alkoxy, hydroxyl, and aryloxy;
R is independently selected from hydrogen, $C_1$ to $C_{20}$ alkyl, $C_3$ to $C_{20}$ cycloalkyl, and $C_6$ to $C_{18}$ aryl;
$R^1$ is independently selected from $C_1$ to $C_{20}$ alkyl, $C_3$ to $C_{20}$ cycloalkyl, hydroxyalkyl, and hydroxycycloalkyl;
y is an integer from 0 to 4,
w is an integer from 0 to 2, and
x is an integer from 1 to 3, with the proviso that when w is 0, y is an integer from 1 to 4 and x is an integer from 2 to 3 and when y is 0, w is an integer from 1 to 2 and x is an integer from 1 to 3.

9 Claims, No Drawings

AMINOPLAST CURABLE COMPOSITIONS CONTAINING DISULFONIC ACID ESTERS AS LATENT ACID CATALYSTS

BACKGROUND OF THE INVENTION

The present invention relates to the use of latent acid catalysts in resinous compositions.

Many industrially desirable coating compositions are capable of acid catalyzed crosslinking. The acid catalyst accelerates crosslinking and thereby reduces the overall time required for cure. When an acid catalyst is utilized, it is advantageous to have the catalyst present as the free acid since in this manner a rapid cure can be efficiently achieved. However, the presence of the free acid may also cause problems in storage stability; that is, the coating composition will exhibit a tendency to gel and harden during the storage term becoming unfit for use.

As a means of circumventing these difficulties, latent or blocked acid catalysts are often utilized to delay the action of crosslinking agents and otherwise postpone the curing mechanism.

Latent acid catalysts are formed by preparing a derivative of an acid catalyst such as para-toluenesulfonic acid (pTSA) or other sulfonic acids. For example, a well-known group of blocked acid catalysts are amine salts of aromatic sulfonic acids, such as pyridinium para-toluenesulfonate. Such sulfonate salts are less active than the free acid in promoting crosslinking. During cure, the catalysts are activated by heating which results in liberation of the free sulfonic acid catalyst.

SUMMARY OF THE INVENTION

In accordance with the present invention there is provided an improved curable composition capable of acid-catalyzed crosslinking comprising an active hydrogen-containing resin, a curing agent present externally and/or internally as a part of the active hydrogen-containing resin, and a catalytic amount of a sulfonate as latent acid catalyst. The catalyst is represented by the following structural formula:

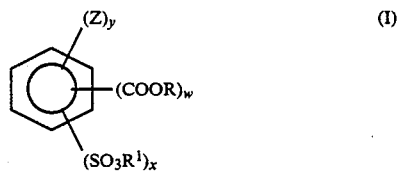

wherein:
  Z is a radical independently selected from $C_1$ to $C_{20}$ alkyl, $C_3$ to $C_{20}$ cycloalkyl, $C_6$ to $C_{18}$ aryl, halogen, alkoxy, hydroxyl, and aryloxy;
  R is independently selected from hydrogen, $C_1$ to $C_{20}$ alkyl, $C_3$ to $C_{20}$ cycloalkyl, and $C_6$ to $C_{18}$ aryl;
  $R^1$ is independently selected from $C_1$ to $C_{20}$ alkyl, $C_3$ to $C_{20}$ cycloalkyl, hydroxyalkyl, and hydroxycycloalkyl;
  y is an integer from 0 to 4,
  w is an integer from 0 to 2, and
  x is an integer from 1 to 3, with the proviso that when w is 0, y is an integer from 1 to 4 and x is an integer from 2 to 3 and when y is 0, w is an integer from 1 to 2 and x is an integer from 1 to 3.

DETAILED DESCRIPTION OF THE INVENTION

The latent acid catalysts of the present invention can be represented by the following structural formula:

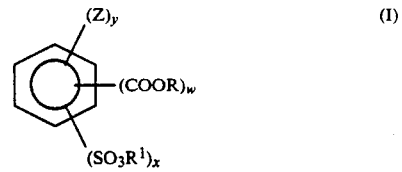

In the above formula (I) Z includes hydroxyl, $C_1$ to $C_{20}$ akyl radicals, $C_3$ to $C_{20}$ cycloalkyl radicals, $C_6$ to $C_{18}$ aryl radicals, halogen radicals, alkoxy radicals and aryloxy radicals. The aforesaid aliphatic, cycloaliphatic, aromatic, and heterocyclic radicals can be substituted with a variety of substituents so long as the substituents do not detract from the properties of the latent acid catalyst. Exemplary of radicals represented by Z include methyl, ethyl, isopropyl, pentyl, hexyl, cyclopentyl, cyclohexyl, phenyl, chloro, methoxy, ethoxy, butoxy, and benzoyloxy. Preferably Z is methyl.

R includes hydrogen, $C_1$ to $C_{20}$ alkyl, $C_3$ to $C_{20}$ cycloalkyl, and $C_6$ to $C_{18}$ aryl. These radicals may also be further substituted with a variety of substituents so long as they do not detract from the properties of the latent acid catalyst. Suitable representative alkyl, cycloalkyl and aryl groups include butyl, hexyl, cyclopentyl, cyclohexyl, cycloheptyl, and phenyl. Preferably R is cyclohexyl. $R^1$ includes $C_1$ to $C_{20}$ alkyl groups, $C_3$ to $C_{20}$ cycloalkyl groups, hydroxyalkyl groups and hydroxycycloalkyl groups. Suitable representative groups include hydroxyethyl, hydroxypropyl, hydroxybutyl, hydroxycyclopentyl, hydroxycyclohexyl as well as the alkyl and cycloalkyl groups detailed above which are representative of R. Preferably $R^1$ is cyclohexyl. In the above formula (I) y is an integer from 0 to 4, preferably 1 to 2, x is an integer from 1 to 3, preferably 2, and w is an integer from 0 to 2, preferably 1.

Exemplary of specific preferred latent acid catalysts according to the present invention include dicyclohexyl toluene-2,4-disulfonate, dicyclohexyl 1,3-xylene-4,6-disulfonate, and tricyclohexyl 3,5-disulfonylbenzoate. It should be understood that although these isomers are most prevalent, other position isomers are also formed.

The latent acid catalysts of the present invention can be produced from the reaction of an alcohol and a disulfonic acid dichloride or disulfobenzoyl acid trichloride, such as toluene-2,4-disulfonyl dichloride, 1,3-xylene-4,6-disulfonyl dichloride and 3,5-bis(chlorosulfonyl)-benzoyl chloride in the presence of an organic solvent and an acid acceptor. In one embodiment the latent catalysts of the present invention can be produced from an aromatic disulfonic acid and an epoxide. Examples of suitable alcohols include 2-butanol, 2-propanol, 1,2-butanediol, 2-hexyloxyethanol, cyclopentanol, and cyclohexanol. Suitable solvents include methylene chloride, toluene, and xylene. Exemplary of suitable acid acceptors include pyridine, triethylamine, sodium hydroxide, potassium hydroxide, sodium methoxide, sodium metal, sodium hydride, potassium hydride, and potassium t-butoxide.

The use of the latent acid catalysts of the present invention in curable compositions is novel and advantageous. Curable compositions cured in the presence of these catalysts result in cured films which exhibit good gloss, hardness, and solvent resistance. Moreover, the curable compositions containing these catalysts exhibit improved package stability.

The curable compositions useful with the latent acid catalysts of the present invention are capable of acid catalyzed crosslinking and comprise in addition to the catalyst an active hydrogen-containing resin, and a crosslinking agent present externally and/or internally as a part of the active hydrogen-containing resin. The active hydrogen-containing resin is preferably a polymeric polyol having an acid value within the range of from 0 to about 160 and a hydroxyl number ranging from about 48 to about 435. Examples of useful polymeric polyols include polyester polyols and acrylic polyols, polyether polyols, and polyurethane polyols. These polyols are described in detail in U.S. Pat. No. 4,154,891, column 3, lines 25 to 68, column 4, lines 1 to 68, column 5, lines 1 to 68, and column 6, lines 1 to 2 which disclosure is incorporated by reference herein.

The aforedescribed polyols require a crosslinking or curing agent to cure to a durable film. The crosslinking agent may be present externally or internally as part of the active hydrogen-containing resin. Examples of external curing agents are aminoplast resins and phenoplast resins, with the aminoplast resins being preferred. The aforesaid external crosslinking agents are described in detail in U.S. Pat. No. 3,919,351, column 5, lines 34 to 68 and column 6, lines 1 to 32 which disclosure is incorporated herein by reference.

The curing agent can also be part of the hydrogen-containing resin. Examples of resins of this type are interpolymers of an N-alkoxymethyl substituted unsaturated carboxylic acid amide with at least one other monomer having a $CH_2=C<$ group, said interpolymers being characterized by having amido hydrogen atoms replaced by the structure $-RCHOR_1$, wherein R is selected from the group consisting of hydrogen and saturated lower aliphatic hydrocarbon radicals and $R_1$ is a member of the class consisting of hydrogen and lower alkyl radicals with the proviso that the interpolymers have a hydroxyl number of at least 10. In general, these interpolymers can be produced in two ways. In the first method, the unsaturated carboxylic acid amide chosen is an N-alkoxymethyl acrylamide (i.e., a material having an $-NHRCHOR_1$ group in the molecule). This N-alkoxymethyl acrylamide is then polymerized with at least one other monomer having a $CH_2=C<$ group to produce a useful interpolymer. In the second method, an unsaturated carboxylic acid amide, e.g., acrylamide is polymerized with at least one other monomer having a $CH_2=C<$ group and is then reacted with an aldehyde to form a useful interpolymer.

Examples of useful interpolymers and their method of manufacture are disclosed in U.S. Pat. Nos. 2,978,437; 3,037,963 and 3,079,434.

Additionally useful herein are a class of interpolymers of N-alkoxymethyl substituted unsaturated carboxylic acid amides, especially N-alkoxymethyl acrylamides as described above, with polyethylenically unsaturated polyesters. The amido nitrogens of such an interpolymer are replaced by the structure $-RCHOR_1$, wherein R can be hydrogen or saturated lower aliphatic hydrocarbon radicals and $R_1$ can be hydrogen or a $C_1-C_{10}$ aliphatic hydrocarbon radical. Any number of unsaturated polyesters may be utilized so long as they are polyethylenically unsaturated.

Both of the aforesaid classes of interpolymers are capable of crosslinking without the necessity of adding external crosslinking resin. It is noted that although an external crosslinking resin is not necessary for those aforedescribed interpolymers capable of internal crosslinking, satisfactory results are attainable if an external curing agent is also added. For this purpose, the aminoplast and phenoplast crosslinking resins described above can be utilized.

When added externally, the crosslinking resin is usually present in an amount of from about 10 percent to about 90 percent by weight based on the total weight of the resinous components of composition. When the curing agent is present internally it is usually present in an amount of from about 5 to 95 percent by weight of the interpolymer, the percentages being based upon the total weight of the resinous composition.

The latent acid catalysts of the claimed invention are utilized in a catalytic amount; that is, an amount sufficient to accelerate the cure of a coating composition to a commercially acceptable rate. Typically, the catalyst is present in an amount ranging from about 0.1 percent to about 20 percent by weight based on the total weight of the resinous components of composition.

In addition to the aforedescribed components, the curable compositions of the present invention ordinarily contain other optional ingredients such as pigments, fillers, plasticizers, flow control agents and other formulating additives. The compositions are typically contained in a solvent which can be any solvent or solvent mixture in which the materials employed are compatible and soluble to the desired extent. For example, suitable solvents include methyl amyl ketone, xylene, toluene, methyl ethyl ketone, methyl isobutyl ketone, ethylene glycol monoethyl ether, and ethylene glycol monobutyl ether.

The curable compositions herein can be applied in any conventional manner, including brushing, flow coating, spraying, and the like. They are preferably intended for application on metallic substrates such as steel or aluminum, primed or unprimed, although they can readily be applied over any substrate.

The curable compositions of the present invention can be cured thermally, whereupon heating, the liberation of the free acid catalyst occurs. The temperature utilized for cure of the claimed compositions varies widely depending upon the particular catalyst and resin system chosen. Typically temperatures between about 60° C. and about 200° C. are utilized, preferably between about 100° C. and 170° C. The length of time for cure can also vary widely, however, from about 20 to 90 minutes is typical.

In addition to use in coating compositions, the latent acid catalysts of the present invention are also useful in other curable compositions such as molding and laminating compositions.

The following examples are submitted for the purpose of further illustrating the nature of the present invention and should not be construed as a limitation on the scope thereof. All parts and percentages in the Examples are by weight unless otherwise indicated.

EXAMPLE I

Preparation of dicyclohexyl 1,3-xylene-4,6-disulfonate

Into a one liter, four-necked, round bottom flask, equipped with stirrer, condenser and thermometer, 100.0 parts of pyridine and 16.55 parts of cyclohexanol were mixed under a nitrogen atmosphere and chilled to 0° C. with an ice water bath. To this solution 25.0 parts of 1,3-xylene-4,6-disulfonyl dichloride were added in portions over thirty minutes. The solution was stirred for one hour at 0° C. and then allowed to stand for twenty-four hours at 15° C. The mixture was poured into one liter of ice water and subsequently extracted with 300 parts of methylene chloride. The organic layer was washed successively with cold 6N sulfuric acid (until the water layer was acidic to pH paper), dilute sodium bicarbonate (three times with 300 part-portions), and water (twice with 300 part-portions). It was then dried over sodium sulfate, filtered, and the solvent removed in vacuo to yield the dicyclohexyl 1,3-xylene-4,6-disulfonate.

EXAMPLE II

Preparation of dicyclohexyl toluene-2,4-disulfonate

Into a one liter, four-necked, round bottom flask, equipped with stirrer, condenser and thermometer, 200.0 parts of pyridine and 20.0 parts of cyclohexanol were mixed under a nitrogen atmosphere and chilled to 0° C. with an ice water bath. To this solution 28.9 parts of p-toluene-2,4-disulfonyl dichloride were added in portions over thirty minutes. The solution was stirred for one hour at 0° C. and then allowed to stand for twenty-four hours at 15° C. The mixture was poured into one liter of ice water and subsequently extracted with 700 parts of methylene chloride. The organic layer was washed successively with cold 6N sulfuric acid (until the water layer was acidic to pH paper), dilute sodium bicarbonate (three times with 500 part-portions), and water (twice with 500 part-portions). It was then dried over sodium sulfate, filtered, and the solvent removed in vacuo to yield the dicyclohexyl toluene-2,4-disulfonate.

EXAMPLE III

This example illustrates some physical properties of cured films of a coating composition incorporating the catalysts prepared in Examples I and II, above. The base coating composition employed was prepared in the following manner:

| | Parts by Weight | Percent of Resin Solids |
|---|---|---|
| Pigment Paste (1) | 563 | 37 |
| Acrylic Resin (2) | 160 | 37 |
| Crosslinking Agent (3) | 86 | 26 |
| Silicone Surfactant (4) | 13 | |
| Methyl Amyl Ketone | 55 | |
| CELLOSOLVE ACETATE (5) | 10 | |

(1) This pigment paste having a 22 percent resin solids content was formulated by combining together: 500 parts of titanium dioxide pigment; 282 parts of acrylic resin (78 percent resin solids content in methyl amyl ketone, commercially available from Rohm and Haas as ACRYLOID AT-400); 145 parts of butanol; and 73 parts of methyl amyl ketone.
(2) This thermosetting acrylic resin has a 78 percent resin solids content in methyl amyl ketone and a hydroxyl number of 67. It is commercially available from Rohm and Haas as ACRYLOID AT-400.
(3) Melamine-formaldehyde resin is commercially available as CYMEL 303 from American Cyanamid.
(4) Silicone surfactant (1% in toluene) is commercially available as S.F. 1023 from General Electric Corp.
(5) Commercially available from Union Carbide Corp.

The catalyst containing compositions were formulated by adding 1 percent by weight of the catalysts to the aforedescribed base coating composition (38 percent resin solids).

Each coating composition was applied with a 3 mil drawbar to steel panels pretreated with BONDERITE 500 (treated panels available from Hooker Chemical Co).

Sward Hardness was calculated by averaging two separate readings.

The solvent resistance was evaluated after each panel underwent 20 double rubs with xylene. Ratings were as follows:
10—no effect
9–6—gloss marred
5—slight removal of film
4–1—increased film removal
0—complete film removal
Gloss was measured with a gloss meter.

| | Cured at 120° C. | | | | | | Cured at 135° C. | | | | | |
|---|---|---|---|---|---|---|---|---|---|---|---|---|
| | 15 minutes | | | 30 minutes | | | 15 minutes | | | 30 minutes | | |
| Catalyst (1% active catalyst) by weight | Sward Hardness | Xylene Resistance | Gloss/60° | Sward Hardness | Xylene Resistance | Gloss/60° | Sward Hardness | Xylene Resistance | Gloss/60° | Sward Hardness | Xylene Resistance | Gloss/60° |
| para-toluenesulfonic acid | 36 | 9 | 65 | 41 | 9 | 70 | 27 | 8 | 67 | 32 | 8 | 75 |
| dicyclohexyl toluene-2,4-disulfonate | 27 | 6 | 80 | 24 | 9 | 75 | 32 | 6 | 78 | 34 | 7 | 77 |
| dicyclohexyl 1,3-xylene-4,6-disulfonate | 24 | 9 | 80 | 36 | 8 | 80 | 31 | 8 | 84 | 40 | 9 | 80 |

EXAMPLE IV

Preparation of tricyclohexyl 3,5-disulfonylbenzoate

Into a one liter, four-necked, round bottom flask equipped with stirrer, condenser, and thermometer 142.2 parts of pyridine and 100.16 parts of cyclohexanol were mixed under a nitrogen atmosphere and chilled to 0° C. with an ice water bath. To this solution were added slowly in small amounts over a period of one hour while maintaining the temperature between 0° and 10° C., 54.5 parts of 3,5-bis(chlorosulfonyl)benzoyl chloride* dissolved in 200.0 parts of methylene chloride. The mixture was stirred and then allowed to stand for 30 minutes at 0° C. Subsequently, the reaction mixture was refrigerated prior to workup.

*The 3,5-bis(chlorosulfonyl)benzoyl chloride was prepared in the following manner: Into a three-liter, round bottom flask equipped with a glass stirrer with TEFLON paddle, thermometer, condenser, and air aspirator were charged 152.4 grams of moist disodium 3,5-disulfonatobenzoic acid and 416.4 grams of phosphorus pentachloride. The mixture was warmed slowly to 110° C. and refluxed for 10 hours. A total of 21 grams of liquid was distilled off to a pot temperature of 140° C. The reaction mixture was then cooled to 0° C. and quenched with 200 grams of ice water. Subsequently, 300 grams of methylene chloride were added and the solution was stirred for one hour. The methylene chloride layer was then separated, washed once with cold water (300 grams), dried over magnesium sulfate and filtered. The resultant yellow solution was concentrated in vacuo to yield the 3,5-bis(chlorosulfonyl)-benzoyl chloride product as a yellow crystalline product having a melting point within the range of 85° C. to 87° C.

For workup, the reaction mixture was cooled to 0° C., poured into 500 parts of ice water, and extracted with 300 parts of methylene chloride. The organic layer was washed successively with cold, dilute sulfuric acid (twice); cold dilute sodium bicarbonate (once); and water until the water layer was neutral to pH paper. (Emulsion formation during the water washing required addition of 5 percent potassium chloride to assist in breaking the emulsion. This was not completely effective and it was necessary to let the emulsion separate over a few days followed by additional water washings and potassium chloride addition.) It was then dried over sodium sulfate, filtered, and the solvent removed in vacuo to yield the tricyclohexyl 3,5-disulfonylbenzoate.

EXAMPLE V

In this example the tricyclohexyl 3,5-disulfonylbenzoate catalyst prepared in Example IV, above, was incorporated into the base coating composition prepared in Example III, above. The cured film was evaluated for hardness and chemical resistance.

The catalyst containing composition was prepared by adding 1 percent by weight of the tricyclohexyl 3,5-disulfonylbenzoate to the aforedescribed base coating composition (38 percent resin solids).

The coating composition was applied with a 3 mil drawbar to steel panels pretreated with BONDERITE 5000 (treated panels available from Hooker Chemical Co.). The panels were baked at 250° F. (121° C.) for 30 minutes resulting in a hard (5H Pencil Hardness), glossy film with excellent solvent resistance.

Solvent Resistance was evaluated as described in Example III, above. An "excellent" rating indicated that the coating was unaffected by the xylene rubs.

Pencil Hardness was a measure of the resistance of the coating to a pencil indentor. The hardness scale is as follows beginning with 4B which indicates a relatively soft coating and increasing to 10 H which indicates a relatively hard coating:

4B, 3B, 2B, B, HB, F, H, 2H, 3H . . . up to 10H.

EXAMPLE VI

This example illustrates hot room stabilities of selected latent acid catalysts of the claimed invention. Stability was based upon the length of time required for a sample of the coating composition described in Example III, above, containing catalyst, to double in viscosity while in a hot room at 49° C. Each sample contained 1 percent catalyst by weight.

| Catalyst | Time to Double in Viscosity at 49° C. |
| --- | --- |
| None (control) | Greater than 4 weeks |
| para-toluenesulfonic acid | Less than 1 day |
| dicyclohexyl 1,3-xylene-6-disulfonate | 1 day |
| dicyclohexyl toluene-2,4-disulfonate | 2 days |
| tricyclohexyl 3,5-disulfonylbenzoate | 2 days |

What is claimed is:

1. In a curable composition capable of acid catalyzed crosslinking, comprising an active hydrogen-containing resin, a curing agent present externally and/or internally as a part of the active hydrogen-containing resin, and an acid catayst, wherein the improvement comprises using as the acid catalyst a catalytic amount of a sulfonate represented by the following structural formula:

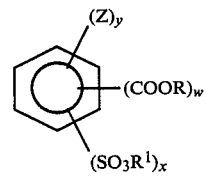

wherein:
Z is a radical independently selected from $C_1$ to $C_{20}$ alkyl, $C_3$ to $C_{20}$ cycloalkyl, $C_6$ to $C_{18}$ aryl, halogen, alkoxy, hydroxyl, and aryloxy;
R is independently selected from hydrogen, $C_1$ to $C_{20}$ alkyl, $C_3$ to $C_{20}$ cycloalkyl, and $C_6$ to $C_{18}$ aryl;
$R^1$ is independently selected from $C_1$ to $C_{20}$ alkyl, $C_3$ to $C_{20}$ cycloalkyl, hydroxyalkyl, and hydroxycycloalkyl;
y is an integer from 0 to 4,
w is an integer from 0 to 2, and
x is an integer from 1 to 3, with the proviso that when w is 0, y is an integer from 1 to 4 and x is an integer from 2 to 3 and when y is 0, w is an integer from 1 to 2 and x is an integer from 1 to 3.

2. The curable composition of claim 1 wherein Z is $C_1$ to $C_{20}$ alkyl and $R^1$ is $C_3$ to $C_{20}$ cycloalkyl.

3. The curable composition of claim 2 wherein y is 1.

4. The curable composition of claim 2 wherein y is 2.

5. The curable composition of claim 3 wherein the sulfonate is dicyclohexyl toluene 2,4-disulfonate.

6. The curable composition of claim 4 wherein the sulfonate is dicyclohexyl 1,3-xylene-4,6-disulfonate.

7. The curable composition of claim 1 wherein R is $C_3$ to $C_{20}$ cycloalkyl, $R^1$ is $C_3$ to $C_{20}$ cycloalkyl.

8. The curable composition of claim 7 wherein the sulfonate is tricyclohexyl 3,5-disulfonylbenzoate.

9. The curable composition of claim 1 wherein the amount of latent acid catalyst ranges from about 0.1 percent by weight to about 20 percent by weight based on the resinous components of the composition.

* * * * *